US006242614B1

(12) United States Patent
Vemishetti et al.

(10) Patent No.: US 6,242,614 B1
(45) Date of Patent: Jun. 5, 2001

(54) SEMI-SYNTHESIS OF PACLITAXEL USING DIALKYLDICHLOROSILANES

(75) Inventors: Purushotham Vemishetti, East Syracuse, NY (US); Francis S. Gibson, Dayton, NJ (US); John L. Dillon, East Syracuse, NY (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 09/579,184

(22) Filed: May 25, 2000

Related U.S. Application Data

(60) Provisional application No. 60/136,559, filed on May 28, 1999.

(51) Int. Cl.$^7$ .................... C07D 305/00; C07D 407/00
(52) U.S. Cl. .......................... 549/214; 549/510
(58) Field of Search ...................... 549/214, 510

(56) References Cited

U.S. PATENT DOCUMENTS

| Re. 34,277 | 6/1993 | Denis et al. | 549/510 |
|---|---|---|---|
| 5,274,124 | 12/1993 | Holton | 549/214 |
| 5,770,745 | 6/1998 | Swindell et al. | 549/510 |
| 6,005,120 * | 12/1999 | Holton et al. | 549/220 |
| 6,090,951 * | 7/2000 | Poss et al. | 549/214 |
| 6,136,808 * | 10/2000 | Abe et al. | 514/255 |
| 6,136,988 * | 10/2000 | Murray et al. | 549/510 |
| 6,136,990 * | 10/2000 | Mandai et al. | 549/510 |
| 6,150,537 * | 10/2000 | Liotta et al. | 549/214 |
| 6,156,789 * | 12/2000 | Bissery et al. | 514/449 |

FOREIGN PATENT DOCUMENTS

| 534 707-B1 | 12/1996 | (EP) | C07D/305/14 |
|---|---|---|---|
| 400 971-B1 | 7/1998 | (EP) | C07D/205/08 |
| WO 93/06079 | 4/1993 | (WO) | C07C/229/08 |

OTHER PUBLICATIONS

Kingston et al., Tetrahedron Letters, vol. 35, No. 26, pp. 4483–4484 (1994).
Craig et al., Tetrahedron Letters, vol. 33, No. 41, pp. 6165–6168 (1992).
Hutchinson et al., Tetrahedron Letters, vol. 32, No. 5, pp. 573–576 (1991).
Craig et al., Tetrahedron Letters, vol. 31, No. 45, pp. 6585–6588 (1990).
Commercon et al., Tetrahedron Letters, vol. 33, No. 36, pp. 5185–5188 (1992).
Craig et al., Tetrahedron Letters, vol. 33, No. 28, pp. 4073–4076 (1992).
Denis et al., J. Am. Chem. Soc., vol. 110, pp. 5917–5919 (1988).
Gillard et al., J. Org. Chem., vol. 53, pp. 2602–2608 (1988).
Grotli et al., J. Chem. Soc. Chem. Commun., pp. 495–497 (1995).
Bradford et al., Tetrahedron Letters, vol. 36, No. 24, pp. 4189–4192 (1995).
Colombier et al., Tetrahedron Letters, vol. 35, No. 44, pp. 8167–8170 (1994).

* cited by examiner

*Primary Examiner*—Deborah C. Lambkin
(74) *Attorney, Agent, or Firm*—Gabriel Lopez; Timothy J. Babcock

(57) ABSTRACT

A process for the synthesis of paclitaxel from 10-deacetylbaccatin-III which is protected at the 7-position with a dialkylalkoxysilyl protecting group having the formula —Si(R)$_2$(OR').

13 Claims, No Drawings

SEMI-SYNTHESIS OF PACLITAXEL USING DIALKYLDICHLOROSILANES

RELATED APPLICATIONS

This application claims priority benefit under title 35 § 119(e) of U.S. Provisional Application No. 60/136,559, filed May 28, 1999, and entitled SEMI-SYNTHESIS OF PACLITAXEL USING DIALKYLDICHLOROSILANES, the entire contents of which are incorporated herein by reference.

BRIEF DESCRIPTION OF THE INVENTION

The present invention is directed to the synthesis of paclitaxel from 10-deacetylbaccatin-III which is protected at the 7-position with a dialkylalkoxysilyl protecting group.

BACKGROUND & SUMMARY OF THE INVENTION

Paclitaxel (Taxol®), a diterpene taxane compound, is a natural product extracted from the bark of the Pacific yew tree, *Taxus Brevifolia*. It has been shown to have excellent antitumor activity in in vivo animal models, and recent studies have elucidated its unique mode of action, which involves abnormal polymerization of tubulin and disruption of mitosis during the cell cycle. Taxol has recently been approved for the treatment of refractory advanced ovarian cancer, breast cancer and most recently, AIDS-related Kaposi's Sarcoma. The results of paclitaxel clinical studies are replete in scientific periodicals and have been reviewed by numerous authors, such as Rowinsky and Donehower in The Clinical Pharmacology and Use of Antimicrotubule Agents in Cancer Chemotherapeutics, *Pharmac. Ther.*, 52, pp. 35–84 (1991); Spencer and Faulds, Paclitaxel, A Review of its Pharmacodynamic and Pharmacokinetic Properties and Therapeutic Potential in the Treatment of Cancer, *Drugs*, 48 (5), pp. 794–847 (1994); K. C. Nicolau et al., Chemistry and Biology of Taxol, *Angew. Chem., Int. Ed. Eng.*, 33, pp. 15–44 (1994); F. A. Holmes, A. P. Kudelka, J. J. Kavanaugh, M. H. Huber, J. A. Ajani, and V. Valero, "Taxane Anticancer Agents—Basic Science and Current Status", edited by Gunda I Georg, Thomas C. Chen, Iwao Ojima, and Dolotrai M. Vyas, pp. 31–57 American Chemical Society, Wash., D.C. (1995); Susan G. Arbuck and Barbara Blaylock, "Taxol® Science and Applications", edited by Matthew Suffness, pp. 379–416, CRC Press, Boca Raton, Fla. (1995) and the references cited therein.

Commercial pharmaceutical products containing paclitaxel are available, e.g. for the treatment of ovarian and breast cancer, and most recently, AIDS-related Kaposi's Sarcoma. Paclitaxel has also shown promising results in clinical studies for the treatment of other cancers. As a result, the demand for paclitaxel continues to escalate, and ever increasing amounts of paclitaxel are needed with each passing year for continued research and clinical studies. Paclitaxel is extracted with difficulty and in low yields for the bark of *Taxus brevifolia* (approximately 1 kg. of the drug is isolated from the bark of 3,000 *T. brevifolia* trees). Because of the difficulty in extracting adequate yields, alternative sources for synthesizing paclitaxel are needed.

10-deacetylbaccatin-III ("10-DAB") (1, Scheme-1) is currently the starting material for the semi-synthesis of paclitaxel, and may be readily extracted from the needles and twigs of the European Yew tree, *Taxus baccata* L. 10-DAB does not, however, exhibit the degree of anti-tumor activity demonstrated by paclitaxel. Accordingly, the semi-synthesis of paclitaxel from baccatin III. 10-DAB and other taxane compounds is of great interest and importance.

Three distinct approaches for making paclitaxel are known in the literature. Two approaches utilizes 7-O-TES-baccatin-III (3, Scheme-1) obtained from the selective sylylation and acetylation of 10-DAB (1) (Greene et al., *J. Am. Chem. Soc.* 110, p. 5917 (1988). The first route, developed by Prof. Holton and disclosed in U.S. Pat. No. 5,274,124 (Scheme-2) reacts the lithium anion of 3 with a β-lactam to introduce the required amino acid side chain at the 13-position. The second route developed by Bristol-Myers Squibb Co. and disclosed in U.S. patent application Ser. No. 07/995,443, and by D. G. I. Kingston et al. in Tetrahedron Letters 35, p. 4483 (1994), (Scheme-3) couples 3 with an oxazolinecarboxylic acid ((4S-trans)-4,5-dihydro-2,4-diphenyl-5-oxazolecarboxylic acid) (4) using DCC or similar dehydrating agent. Using DCC, A Commercon et al. at Rhone Poulenc Rhorer (Tetrahedron Letters 33, pp.5185–5188 (1992), have developed a third synthesis of paclitaxel coupling 7-O-Troc-baccatin-III (5) with the protected β-phenylisoserine (6) shown in Scheme-4.

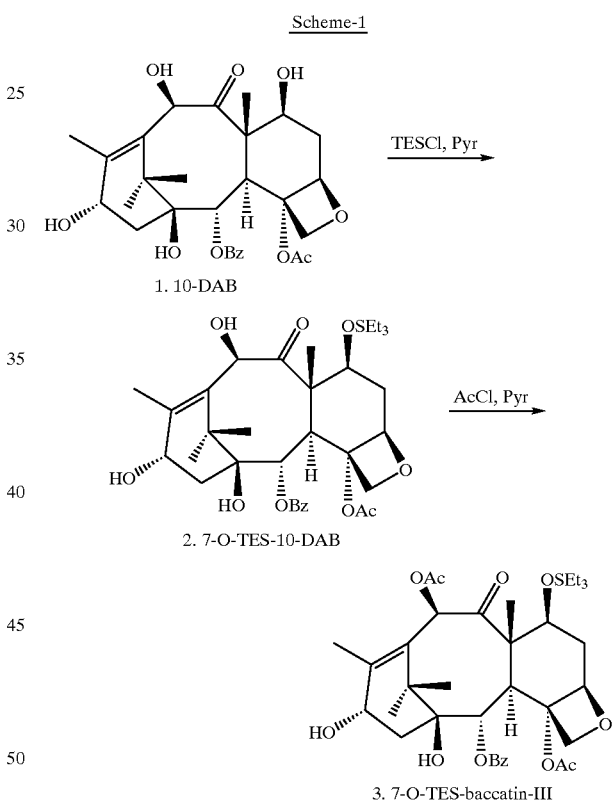

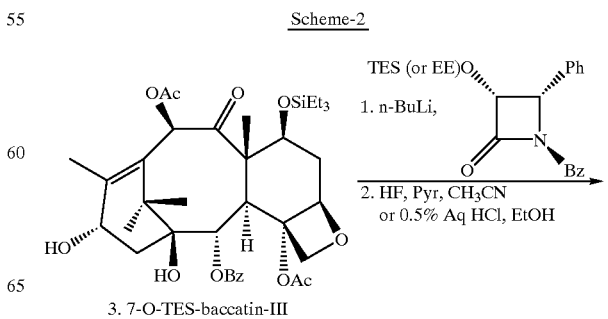

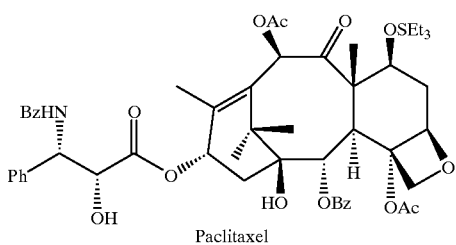

Paclitaxel

Scheme-3

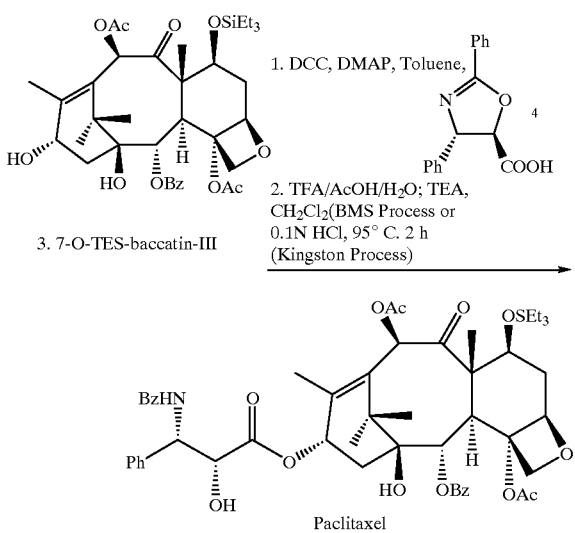

3. 7-O-TES-baccatin-III

1. DCC, DMAP, Toluene, [oxazoline 4]
2. TFA/AcOH/H₂O; TEA, CH₂Cl₂ (BMS Process or 0.1N HCl, 95° C. 2 h (Kingston Process)

Paclitaxel

Scheme-4

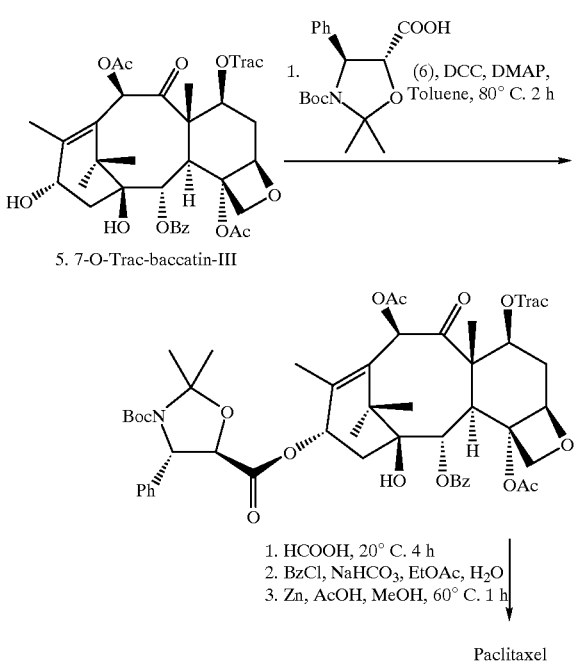

5. 7-O-Trac-baccatin-III 1. (6), DCC, DMAP, Toluene, 80° C. 2 h

1. HCOOH, 20° C. 4 h
2. BzCl, NaHCO₃, EtOAc, H₂O
3. Zn, AcOH, MeOH, 60° C. 1 h

Paclitaxel

DETAILED DESCRIPTION OF THE INVENTION

It is an object of the present invention to provide a rapid, new, useful and efficient protocol for the semi-synthesis of paclitaxel from 7-O protected 10deacetylbaccatin-III derivatives, which generally comprises acetylation at the 10-position, followed by the attachment of a paclitaxel sidechain to the protected 10-deacetylbaccatin-III derivatives, and the subsequent deprotection of the 7-O-protected 10-deacetylbaccatin-III derivatives.

Another object of the present invention is the provision of methods of producing various 10-deacetylbaccatin-III derivatives having a protecting group at the C-7 site on the taxane structure, and which, after attachment of a sidechain and subsequent deprotection, yields paclitaxel in significant amounts.

An additional object of the present invention is the provision of a simple, efficient, and cost effective protocol for the semi-synthesis of paclitaxel.

Accordingly, the present invention encompasses a novel method by which 10-deacetylbaccatin-III can be efficiently converted to 7-O-protected 10-deacetylbaccatin-III using several different protecting groups. After attachment of a paclitaxel sidechain at the C-13 site, these 7-O-protected 10-deacetylbaccatin-III compounds can then be easily converted into paclitaxel making 10-deacetylbaccatin-III a valuable starting material for the semisynthesis of paclitaxel.

The present invention is broadly directed to a chemical process for the rapid and efficient production of paclitaxel, intermediates and precursors thereof. More specifically, the present invention is directed to the semi-synthesis of paclitaxel by protecting the 7-hydroxyl of paclitaxel precursor 10-deacetylbaccatin-III to provide 7-O-protected 10-deacetylbaccatin-III, using dialkyldichlorosilanes, followed by the selective acetylation at the C-10 position, the coupling of a paclitaxel sidechain at the C-13 position, and the subsequent deprotection at the C-7 position and replacement of the protecting group with a hydrogen. More particularly, the invention utilizes diakyldichlorosilane protecting groups such as $Ph_2SiCl_2$ and $i\text{-}Pr_2Cl_2$ at the C-7 site on the taxane during the coupling of the paclitaxel sidechain at the C-13 position.

The general process described herein involves the production of 7-O-protected-10-deacetylbaccatin-III derivatives, such as 7-OS(i-Pr)₂(OMe)-10-deacetylbaccatin-III, selective acetylation at C-10 to form a compound such as, for example, 7-OSi(i-Pr)₂(OMe)-baccatin-III, followed by the coupling of a sidechain at C-13, and the deprotection of the C-13 to form paclitaxel. A particularly advantageous dialkyldichlorosilane protecting group has the generic chemical formula: —Si(R)₂(OR'), where R=Me, Et, i-Pr, Bu, Ph and R'=Me, Et, Pr, i-Pr, t-Bu, $CH_2CF_3$, $CH_2CF_2CH_3$, $CH(CF_3)_2$ and H. Protecting groups are discussed in detail in "Protective Groups in Organic Synthesis", Second Ed., by Theodora W. Greene and Peter G. M. Wuts (1991, John Wiley & Sons, Inc.).

The specific examples which follow illustrate the synthesis of representative compounds of the instant invention and are not to be construed as limiting the invention in sphere or scope. The methods may be adapted to variations in order to produce intermediates and compounds embraced by this invention but not specifically disclosed. Further, variations of the methods to produce the same compounds in somewhat different fashion will also be evident to one skilled in the art.

(I) Silylation: 10-DAB (1) was reacted with a series of dialkyldichlorosilanes (e.g. $Ph_2SiCl_2$ and $i\text{-}Pr_2SiCl_2$) in the presence imidazole in DMF under different reaction temperatures (RT to −53° C.) for 1–3.5 h. The resulting monochlorosilane intermediates were treated with alcohols, such as MeOH, EtOH, i-PrOH, PrOH, t-BuOH, $CF_3CH_2OH$, $CF_3CF_2CH_2OH$, $(CF_3)_2CHOH$ and water. The crude products obtained after workup were purified by either crystallization or chromatography to provide a good yield of 7-O-Si(R)$_2$(OR')-10-DAB (7-23, See Scheme-5). This silylation reaction can also be performed in dimethylacetamide and 1-methyl-2-pyrrolidinone.

Dimethyldichlorosilane behaved differently among five other dialkyldichlorosilanes studied in the silylation of 10-DAB (1). An extensive decomposition of 10-DAB (1) was observed when 10-DAB (1) was treated dimethyldichlorosilane in DMF in the presence of imidazole for 1 h at −33° C. followed by addition of 2-propanol. However, the pre-formed reagent from dimethyldichlorosilane, i.e. chloromethoxydimethysilane was reacted with 1 in the presence of imidazole in DMF and furnished 7-OSiMe$_2$(OMe)-10-DAB (24) in 48.9% yield. Using the preformed reagent approach, 7-OSi(i-Pr)$_2$(OMe)-10-DAB (15) was also prepared from 10-DAB (1) and diisopropylmethoxychlorosilane. The latter reagent was prepared from diisopropyldichlorosilane with method in the presence of triethylamine.

The above silylation study determined the following: (i) The order of reactivity is Me$_2$SiCl$_2$>Et$_2$SiCl$_2$>Pr$_2$SiCl$_2$, n-Bu$_2$SiCl$_2$>i-Pr$_2$SiCl$_2$>Ph$_2$SiCl$_2$; and (ii) Selectivity of diisopropyldichlorosilane to undergo silylation at 7-position of 10-DAB is excellent compared to diethyldichlorosilane, and formation of bis-7,10 or 7,13-O-silylated products are insignificant.

At the outset of this study, silylation of 10-DAB (1) with trialkoxychlorosilanes, such as (EtO)$_3$SiCl was also examined, and 7-O-Si(OEt)$_3$-10-DAB (26) was obtained therefrom in high yield.

(II) Acetylation: Acetylation of a few 7-OSi(R)$_2$(OR')-10-DAB (7–13, 15, 16, 19, 21 and 24) were conducted using LiHMDS and acetyl imidazole at −45 to −25° C. Results are summarized in Scheme-6. The following conclusions are made:

Facile order of acetylation: 7-OSiMe$_2$(OR')>7-OSiEt$_2$(OR')-10-DAB, 7-OSiBu$_2$Si(OR')-10-DAB>7-OSi(i-Pr)$_2$(OR')-10-DAB Decreasing reactivity was observed as the steric bulk of the alcoholic group in 7-OSi(R)$_2$(OR') is increased.

In the case of 7-OSi(i-Pr)$_2$(OMe)-10-DAB (15), acetylation has been examined in DMF and THF. Reactions in DMF were faster, and cleaner.

(III) Paclitaxel: A few acetylated baccatin derivatives were selected for further conversion to paclitaxel using both the BMOP and oxazolinecarboxylic acid sidechain approaches. In the first method, 7-OSiEt$_2$(OCH$_2$CF$_3$)-baccatin-III (32) was coupled with BMOP ((3R-cis)-1-Benzoyl-3-(1-methoxy-1-methylethoxy)-4-phen-yl-2-azetidinone) in anhydrous THF (−55° C., RT, 2 h) as shown in the Scheme-7. The resulting MOP intermediate (39) was hydrolyzed with TFA/AcOH/H$_2$O in 17 h to provide paclitaxel after chromatography.

In the second approach (Scheme-8), four examples (31, 32, 33 and 34) were coupled with (4S-trans)-4,5-dihydro-2,4-diphenyl-5-oxazolecarboxylic acid in the presence of DCC (or DIC) and DMAP in toluene at room temperature for 1–4 h to furnish coupled product in excellent yields. Other activating reagents, such as Morpho CDI, EDDC, EDC and T3P gave incomplete reactions. The coupled products (40–43) were hydrolyzed with TFA/AcOH/water and the O-benzoyl group was migrated to the amine with TEA to furnish paclitaxel in 76:100% yield.

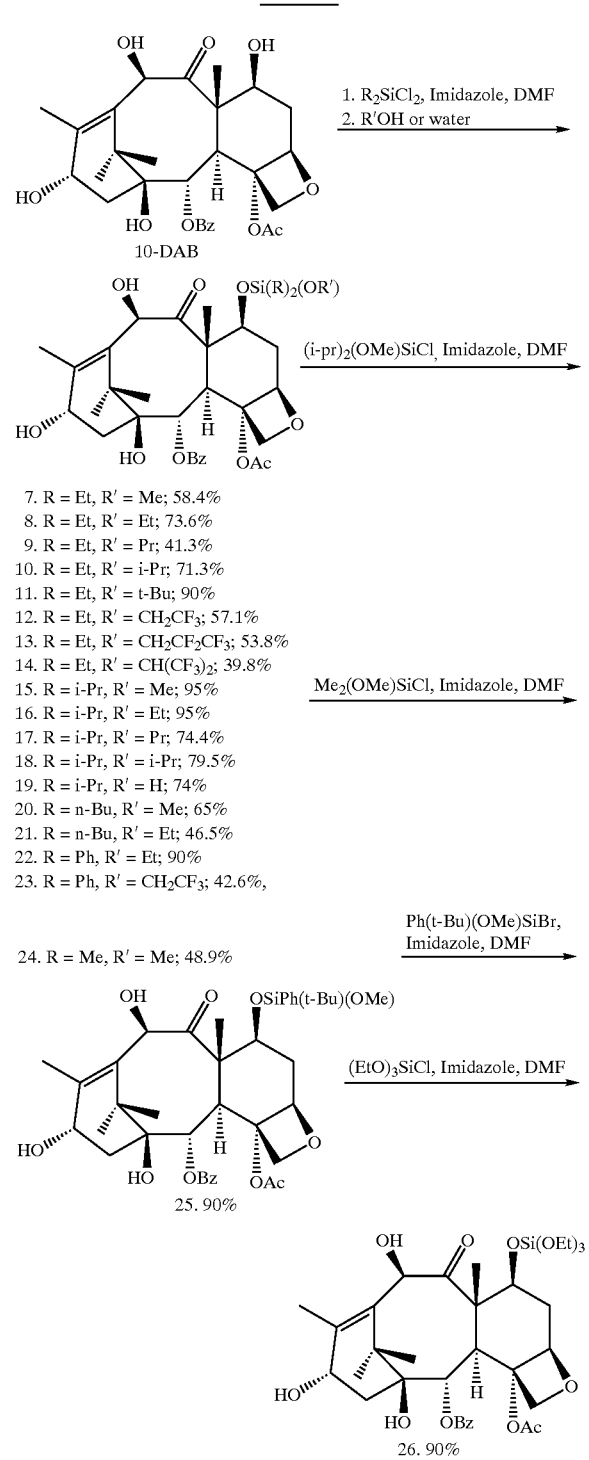

Scheme-5

7. R = Et, R' = Me; 58.4%
8. R = Et, R' = Et; 73.6%
9. R = Et, R' = Pr; 41.3%
10. R = Et, R' = i-Pr; 71.3%
11. R = Et, R' = t-Bu; 90%
12. R = Et, R' = CH$_2$CF$_3$; 57.1%
13. R = Et, R' = CH$_2$CF$_2$CF$_3$; 53.8%
14. R = Et, R' = CH(CF$_3$)$_2$; 39.8%
15. R = i-Pr, R' = Me; 95%
16. R = i-Pr, R' = Et; 95%
17. R = i-Pr, R' = Pr; 74.4%
18. R = i-Pr, R' = i-Pr; 79.5%
19. R = i-Pr, R' = H; 74%
20. R = n-Bu, R' = Me; 65%
21. R = n-Bu, R' = Et; 46.5%
22. R = Ph, R' = Et; 90%
23. R = Ph, R' = CH$_2$CF$_3$; 42.6%,

24. R = Me, R' = Me; 48.9%

25. 90%

26. 90%

Scheme-6

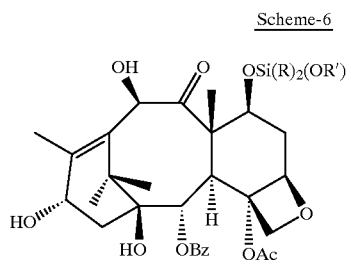

7. R = Et, R' = Me
8. R = Et, R' = Et
9. R = Et, R' = Pr
10. R = Et, R' = i-Pr
11. R = Et, R' = t-Bu
12. R = Et, R' = CH$_2$CF$_3$
13. R = Et, R' = CH$_2$CF$_2$CF$_3$
15. R = i-Pr, R' = Me
16. R = i-Pr, R' = Et
19. R = i=Pr, R' = H
21. R = n-Bu, R' = Et
24. R = Me, R' = Me

1. Acetylimidazole, LiHMDS, THF, −45° C.
2. −25° C. 1,25–6.5 h

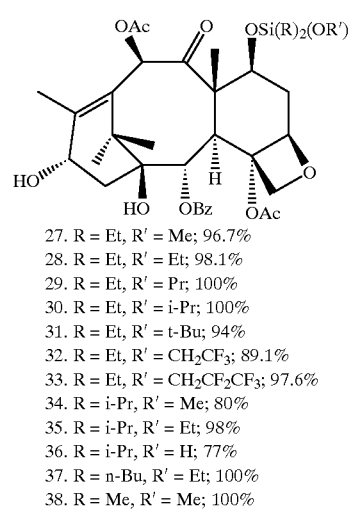

27. R = Et, R' = Me; 96.7%
28. R = Et, R' = Et; 98.1%
29. R = Et, R' = Pr; 100%
30. R = Et, R' = i-Pr; 100%
31. R = Et, R' = t-Bu; 94%
32. R = Et, R' = CH$_2$CF$_3$; 89.1%
33. R = Et, R' = CH$_2$CF$_2$CF$_3$; 97.6%
34. R = i-Pr, R' = Me; 80%
35. R = i-Pr, R' = Et; 98%
36. R = i-Pr, R' = H; 77%
37. R = n-Bu, R' = Et; 100%
38. R = Me, R' = Me; 100%

Scheme-7

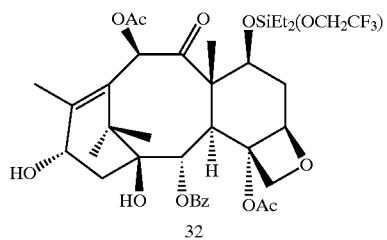
32

1. BMOP, LiHMDS, −55° C., 5 min
2. 2 h, 0° C.

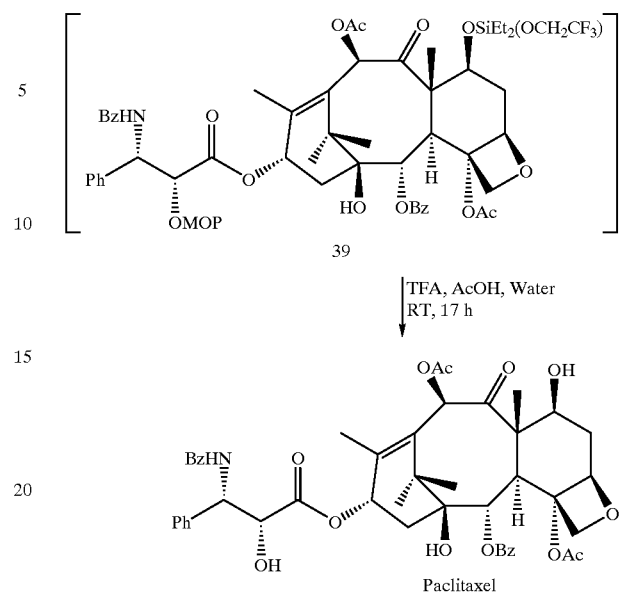
39

TFA, AcOH, Water
RT, 17 h

Paclitaxel

Scheme-8

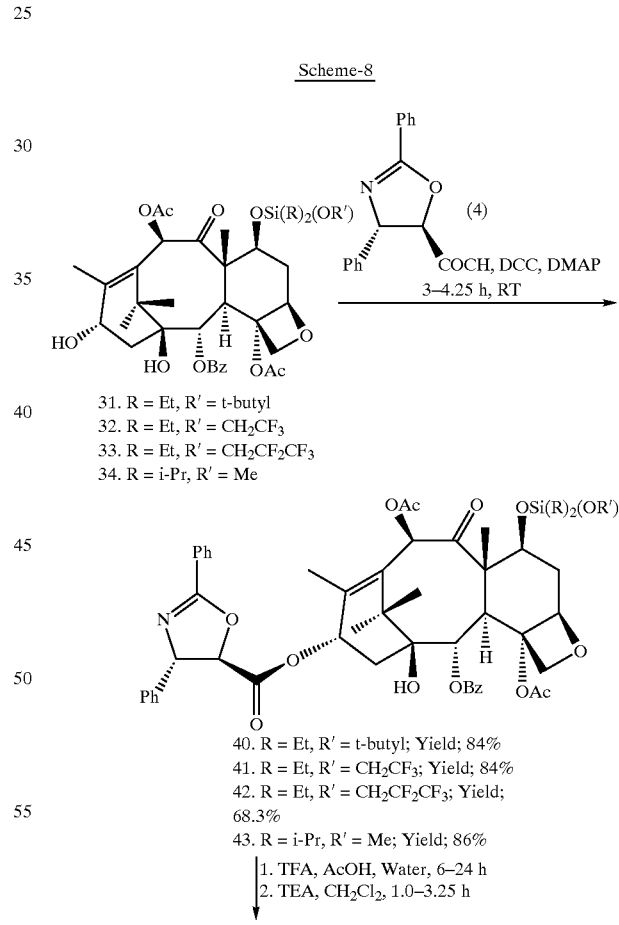

31. R = Et, R' = t-butyl
32. R = Et, R' = CH$_2$CF$_3$
33. R = Et, R' = CH$_2$CF$_2$CF$_3$
34. R = i-Pr, R' = Me 40. R = Et, R' = t-butyl; Yield; 84%
41. R = Et, R' = CH$_2$CF$_3$; Yield; 84%
42. R = Et, R' = CH$_2$CF$_2$CF$_3$; Yield; 68.3%
43. R = i-Pr, R' = Me; Yield; 86%

1. TFA, AcOH, Water, 6–24 h
2. TEA, CH$_2$Cl$_2$, 1.0–3.25 h

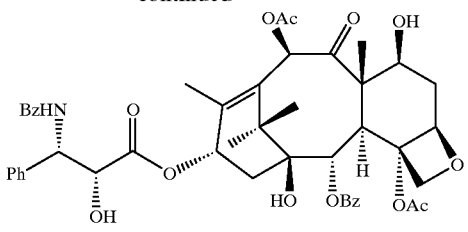

Paclitaxel
Yield: 87% from 40
Yield: 97.4% from 41
Yield: 76.4% from 42
Yield: 76.3% from 43

It is believed that one of ordinary skill in the art can, using the above description perform the processes disclosed and prepare the full scope of the intermediates and compounds of the present invention. The following examples further exemplify the general procedure for the preparation procedures inherent in the synthesis of paclitaxel from 10-deacetylbaccatin-III.

The following examples described the manner and process of making and using the invention and are illustrative rather than limiting. It should be understood that there might be other embodiments that fall within the spirit and scope of the invention as defined by the claims appended hereto. Additionally, the following examples illustrate the invention but should not be interpreted as a limitation thereon.

EXAMPLES

Example 1

General procedure for formation of 7-OSi(R)$_2$(OR')-10-DAB

10DAB is dissolved in DMF. Imidazole was added, and to the resulting solution the dialkyldichlorosilane was added and the disappearance of 10-DAB was monitored by HPLC. When no 10-DAB remains, the appropriate alcohol was added, and the reaction was allowed to stir at rt for 1 hour. The reaction mixture was poured into MTBE, washed 3 times with water and concentrated to give the desired compound.

7-OSiEt$_2$(OMe)-10-DAB (7):

To a stirred solution of 10-DAB (1, 1 g, 1.84 mmol) and imidazole (0.413 g, 6.07 mmol) in dry DMF (12 ml) was added diethyldichlorosilane (0.326 ml, 2.18 mmol) at −53° C. under argon. As thick solids were formed after 10 min, another portion of DMF (6 ml) was added and the stirring was continued for 2 h. Methanol (0.12 ml, 2.96 mmol) was added at −53° C. The reaction was stirred an additional 1 h at −53° C., then allowed to warm to RT over one hour. The reaction mixture was diluted with EtOAc (25 ml), washed with water (4×15 ml), and dried over Na$_2$SO$_4$. Evaporation of the EtOAc gave a foamy solid (1.31 g), which was purified by silica gel chromatography using hexane:EtOAc (3:2) to furnish (0.684 g) in 56.4% yield.

7-OSiEt$_2$(OEt)-10-DAB (8):

To a stirred solution of 10-DAB (1, 1 g, 1.84 mmol) and imidazole (0.413 g, 6.07 mmol) in dry DMF (12 ml) was added diethyldichlorosilane (0.326 ml, 2.18 mmol) at −33° C. under argon. After 2 hr, ethanol (0.173 ml, 2.95 mmol) was added −33° C. The reaction flask was transferred into an ice-bath and stirred for an hour. The reaction mixture was diluted with EtOAc (25 ml), washed with water (4×15 ml) and dried over Na$_2$SO$_4$. Evaporation of the EtOAc gave a foamy solid (1.26 g), which was purified was purified by silica gel chromatography using hexane:EtOAc (3:2) to furnish 8 (0.912 g) in 73.6% yield.

7-OSiEt$_2$(OPr)-10-DAB (9):

Using the procedure described for 8, 10-DAB (1, 0.75 g, 1.38 mmol), diethyldichlorosilane (0.245 ml, 1.64 mmol), imidazole (0.31 g, 4.55 mmol) and propanol (0.165 ml, 2.21 mmol) in dry DMF (9 ml) afforded 9 (0.392 g) in 41.3% yield.

7-OSiEt$_2$(O-i-Pr)-10-DAB (10):

7-OSiEt$_2$(O-i-Pr)-10-DAB (10, 0.902 g) was obtained in 71.3% yield, according to the procedure described for 8, from 10-DAB (1, 1 g, 1.84 mmol), diethyldichlorosilane (0.326 ml, 2.18 mmol), imidazole (0.413 g, 6.07 mmol) and isopropanol (0.226 ml, 2.95 mmol) in dry DMF (12 ml).

7-OSiEt$_2$(O-t-Bu)-10-DAB (11):

Using the general procedure, 1 (250 mg, 0.46 mmol) was reacted with diethyldichlorosilane (0.096 ml, 0.64 mmol) and imidazole (70 mg, 1 mmol) in DMF (3 ml) for 15 min, followed by t-butanol (0.136 g, 1.84 mmol) to produce 11 (0.288 g) in 90% yield.

7-OSiEt$_2$(OCH$_2$CF$_3$)-10-DAB (12):

Diethyldichlorosilane (0.34 ml, 2.27 mmol) was added over 3 min to a stirred solution of 10-DAB (1, 1.044 g, 1.91 mmol) and imidazole (0.431 g, 6.33 mmol) in dry DMF (7 ml) at −20° C., under argon. The reaction was stirred for an hour at −15 to 10° C. The HPLC showed the absence of starting material. Trifluoroethanol (0.22 ml, 3.02 mmol) was added over 2 min to the thick reaction mixture at −10° C. the reaction flask was taken from the acetone-dry ice bath and placed in an ice bath. After an hour of stirring, the reaction mixture was diluted with EtOAc (25 ml), washed with water (4×15 ml), dried over Na$_2$SO$_4$ and evaporated to a foamy solid (1.588 g). Silica gel chromatography using hexane:EtOAc (1:1) furnished 12 (0.798 g) in 57.1% yield.

7-OSiEt$_2$(OCH$_2$CF$_2$CF$_3$)-10-DAB (13):

13 (0.802 g) was prepared in 53.8% yield, using the above procedure for 12, from 10DAB (1, 1.042 g, 1.91 mmol), imidazole (0.341 g, 6.33 mmol), diethyldichlorosilane (0.34 ml, 2.27 mmol), CF$_3$CF$_2$CH$_2$OH (0.31 ml, 3.11 mmol), and dry DMF (7 ml).

7-OSiEt$_2$[OCH(CF$_3$)$_2$]-10-DAB (14):

10-DAB (1, 1.053 g, 1.93 mmol), diethyldichlorosilane (0.343 ml, 2.29 mmol), imidazole (0.435 g, 6.39 mmol), DMF (7 ml) and (CF$_3$)$_2$CHOH (0.321 ml, 3.05 mmol) gave, according to the conditions for 12, 14 (0.613 g) in 39.8% yield after silica gel chromatography using hexane:EtOAc (3:2).

7-OSi(i-Pr)$_2$(OPr)-10-DAB (17):

Diisopropyldichlorosilane (0.4 ml, 2.22 mmol) was added over 3 min to a stirred solution of 10-DAB (1, 1 g, 1.84 mmol) and imidazole (0.413 g, 6.07 mmol) in dry DMF (7 ml) at room temperature under argon and stirred for 3 h. Propanol (0.22 ml, 2.94 mmol) was added to the reaction mixture and stirring was continued for 20 h, the reaction mixture was diluted with EtOAc (25 ml), washed with water (4×15 ml), dried over Na$_2$SO$_4$ and evaporated to a foamy solid (1.415 g). Silica gel chromatography using hexane:EtOAc (3:2) gave 17 (0.98 g) in 74.4% yield.

7-OSi(i-Pr)$_2$(O-i-Pr)-10-DAB (18):

Diisopropyldichlorosilane (0.366 ml, 2.03 mmol) was added over 3 min to a stirred solution of 10-DAB (1, 1 g, 1.84 mmol) and imidazole (0.413 g, 6.07 mmol) in dry DMF (7 ml) at −20° C. under argon and was stirred for 1.5 h. Isopropanol (0.226 ml, 2.95 mmol) was added to the reaction mixture and stirring was continued at 0° C./1.5 h and at RT/16 h. The reaction mixture was diluted with EtOAc (25 ml), washed with water (4×15 ml), dried over $Na_2SO_4$ and evaporated to a foamy solid (1.45 g). Silica gel chromatography using hexane:EtOAc (2:3) gave 18 (1.046 g) in 79.5% yield.

7-OSi(Bu)$_2$(OEt)10-DAB (21):

Dibutyldichlorosilane (0.476 ml, 2.21 mmol) was added over 3 min to a stirred solution of 10-DAB (1, 1 g, 1.84 mmol) and imidazole (0.413 g, 6.07 mmol) in dry DMF (7 ml) at 0° C. under argon and stirred for 1 h. Ethanol (0.173 ml, 2.95 mmol) was added to the reaction mixture at 0° C. The resulting reaction mixture was taken from the ice bath and stirred at room temperature for an hour. The reaction mixture was diluted with EtOAc (25 ml), washed with water (4×15 ml), dried over $Na_2SO_4$ and evaporated to a solid (1.482 g). Silica gel chromatography using hexane:EtOAc (65:35) gave 21 (0.624 g) in 46.5% yield.

7-OSiPh$_2$(OCH$_2$CF$_3$)-10-DAB (23):

To a stirred solution of 10-DAB (1, 140 mg, 0.257 mmol) and imidazole (57.7 mg, 0.85 mmol) in dry DMF (1 ml) was added diphenyldichlorosilane (0.06 ml, 0.29 mmol) at −20° C. under argon. The reaction mixture was warmed to 0° C. in an hour and trifluoroethanol (0.03 ml, 0.41 mmol) was added. As the intermediate was not consumed in the reaction after 3.5 h, another portion of trifluoroethanol (0.03 ml, 0.41 mmol) was added and stirred at room temperature for 18 h. The solid product obtained after usual workup, was chromatographed using hexane:EtOAc (1:1) to give 23 (90.4 mg) in 42.6% yield.

7-OSiMe$_2$(OMe)-10-DAB (24):

Chloromethoxydimethylsilane (90% pure, 0.241 ml, 1.84 mmol) was added over a min to a stirred solution of 10-DAB (1, 0.75 g, 1.38 mmol) and imidazole (0.207 g, 3.04 mmol) in dry DMF (7 ml) at −33° C. under argon. As unreacted 10-DAB was noted after 3 h, another portion of chloromethoxydimethylsilane (0.095 ml, 0.73 mmol) was added and stirred for 0.5 h. The reaction mixture after usual workup and purification by silica gel chromatography using hexane:EtOAc (45:55), gave 24 (0.425 g) in 48.9% yield.

7-OSi(i-Pr)$_2$(OMe)-10-DAB (15):

(i) Using the general procedure, 1 (1 g, 1.84 mmol) was reacted with diisopropyldichlorosilane (0.414 ml, 2.3 mmol) and imidazole (0.375 g, 5.5 mmol) in DMF (7 ml) at 0° C. for 2.5 h, followed by methanol (0.15 ml, 3.7 mmol) to produce 15 (1.2 g) in 95% yield. PMR (CDCl$_3$): δ8.15–7.48 (m, 5H), 5.64 (d, 1H, J=6.8), 5.40 (d, 1H, J=1.8), 4.99 (d, 1H, J=5.7), 4.63 (dd, 1H, J=6.3, 10.4), 4.35 (d, 1H, J=8.6), 4.24 (d, 1H, J=2.2), 4.20 (d, 1H, J=8.6), 4.00 (d, 1H, J=6.8), 3.59 (s, 3H), 2.68–2.59 (m, 1H), 2.35–2.25 (m, 5H), 2.18–1.95 (m, 7H), 1.79 (s, 3H), 1.65 (s, 1H), 1.62 (s, 1H), 1.16–0.90 (m, 18H).

(ii) Additionally, 15 (0.94 g, 87%) could be made by reacting a solution of (MeO)Si(i-Pr)$_2$Cl (0.5 g) with 10-DAB (0.75 g) In DMF (6 ml) with imidazole (0.4 g).

(MeO)Si(i-Pr)$_2$Cl was made in 75% yield (0.73 g) by reacting diisopropyldichlorosilane (1 g, 5.4 mmol) with methanol (0.218 ml, 5.4 mmol) and triethylamine (0.75 mL, 5.4 mmol) in Et$_2$O at rt for 1 h. The reaction mixture was filtered to remove TEA-HCl, and the Et$_2$O was evaporated. The resulting oil was used without further purification, and was shown to be 75% pure by GC.

7-OSi(i-Pr)$_2$(OEt)-10-DAB (16):

Using the general procedure, 1 (250 mg, 0.46 mmol) was reacted with diisopropyldichlorosilane (0.096 ml, 0.552 mmol) and imidazole (0.094 g, 1.38 mmol) in DMF (2 ml) at 0° C. for 1.5 h, followed by ethanol (0.10 ml, 1.84 mmol) to produce 16 (0.306 g) in 95% yield.

7-OSi(i-Pr)$_2$(OH)-10-DAB (19):

Using the general procedure, 1 (250 mg, 0.46 mmol) was reacted with diisopropyldichlorosilane (0.108 ml, 0.598 mmol) and imidazole (0.095 g, 1.38 mmol) in DMF (2 ml) at rt for 1.5 h, followed by water (0.025 ml, 1.38 mmol) to produce 19 (0.238 g) in 74% yield.

7-OSiBu$_2$(OME)-10-DAB (20):

Using the general procedure, 1 (250 mg, 0.46 mmol) was reacted with dibutyldichlorosilane (0.119 ml, 0.552 mmol) and imidazole (0.095 g, 1.38 mmol) in DMF (2 ml) at rt for 1.5 h, followed by methanol (0.040 ml, 0.92 mmol) to produce 20 (0.204 g) in 65% yield.

7-OSiPh$_2$(OEt)-10-DAB (22):

Using the general procedure, 1 (250 mg, 0.46 mmol) was reacted with diphenyldichlorosilane (0.127 g, 0.5 mmol) and imidazole (95 mg, 1.37 mmol) in DMF (2.5 ml) for 15 min followed by ethanol (0.5 mL, 8.5 mmol) to produce 22 (0.314 g) in 90% yield.

7-OSiPh(t-Bu)(OMe)-10-DAB (25):

Using the general procedure, 1 (250 mg, 0.46 mmol) was reacted with tert-butylphenylmethoxy-silylbromide (0.157 ml, 0.69 mmol), imidazole (0.063 g, 0.92 mmol) in DMF (2.5 ml) at rt for 1 h to produce 25 (0.305 g) in 90% yield.

7-OSi(OEt)$_3$-10-DAB (26):

Using the general procedure, 1 (1 g, 1.83 mmol) was reacted with triethoxysilylchloride (0.54 ml, 2.75 mmol) and imidazole (0.25 g, 3.66 mmol) in DMF (12 ml) for 40 min at 0° C. to produce 26 (1.16 g) in 90% yield.

Example 2

A. General Procedure for the acetylation of 7-O-silyl protected 10-DAB compounds LiHMDS in THF (0.7 eq) was added over a minute to a stirred solution of 7-OSi(R)$_2$(OR')-10-DAB in THF under Ar at −45° C. After 10 min, acetylimidazole in THF (9.07%; 2 eq) was added over a min and stirred for 3 min at −45° C. Then, the reaction flask was placed in a cryocooler at −25° C. and stirred at that temperature until the reaction was complete (1.25–6 h). The reaction mixture was diluted with MTBE (15 ml) and washed with 10% NaH$_2$PO$_4$ (2×5 ml), water (2×5 ml) and brine (1×5 ml). The MTBE phase was dried over Na$_2$SO$_4$ and evaporated to give a solid baccatin-III product. Using this procedure, following examples were prepared.

7-OSiEt$_2$(OMe)-baccatin-III (27):

7-OSiEt$_2$(OMe)-10-DAB (7, 125 mg, 0.19 mmol) in THF (3 ml) was subjected for the above acetylation procedure for 6 h to give the title compound (27, 0.129 g) in 96.7% yield.

7-OSiEt$_2$(OEt)-baccatin-III (28):

This compound (140 mg) was obtained in 98.1% yield from 7-OSiEt$_2$(OEt)-10-DAB (8, 134.3 mg, 0.2 mmol) in THF (3 ml) after 2.25 h.

7-OSiEt$_2$(OPr)-baccatin-III (29):

This compound (97 mg) was obtained in a quantitative yield from 7-OSiEt$_2$(OPr)-10-DAB (9, 91 mg, 0.132 mmol) in THF (3 ml) after 6 h.

7-OSiEt$_2$(O-i-Pr)-baccatin-III (30):

7-OSiEt$_2$(O-i-Pr)-10-DAB (10, 141.3 mg, 0.21 mmol in THF (3 ml) after 3 h gave a quantitative yield of 30.

7-OSiEt$_2$(OCH$_2$CF$_3$)-baccatin-III (32):

This compound (137.6 mg) was obtained in 89.1% yield from 7-OSiEt$_2$(OCH$_2$CF$_3$)-10-DAB (12, 146 mg, 0.2 mmol) in THF (2 ml) after 1.25 h.

7-OSiEt$_2$(OCH$_2$CF$_2$CF$_3$)-baccatin-III (33):

7-OSiEt$_2$(OCH$_2$CF$_2$CF$_3$)-baccatin-III (32, 0, 104.8 mg) was received in 97.6% yield from 7-OSiEt$_2$(OCH$_2$CF$_2$CF$_3$)-10-DAB (13, 101.8 mg, 0.13 mmol) in THF (2 ml) after 2 h.

7-OSi(n-Bu)$_2$(OEt)-baccatin-III (37):

The title compound was obtained in a quantitative yield from 7-OSi(n-Bu)$_2$(OEt)-10-DAB (21, 117.6 mg, 0.16 mmol) in THF (3 ml) after 3 h.

7-OSiMe$_2$(OMe)-baccatin-III (38):

7-OSiMe$_2$(OMe)-baccatin-III (38, 162 mg) was obtained in a quantitative yield from 7-OSiMe$_2$(OMe)-10-DAB (24, 150.5 mg, 0.24 mmol) in THF (3 ml) after 1.25 h.

B. General Procedure for the acetylation of 7-O-silyl protected 10-DAB compounds The 7-O-protected compound was dissolved in THF or DMF and cooled to −55° C.; LiHMDS was added, and the reaction mix was stirred for 10 minutes. Acetylimidazole was added, and the reaction mix was warmed to −30 to −25° C. The progress of the reaction was monitored by HPLC, and when complete, the reaction was quenched with methanol and acetic acid, poured into MTBE and washed with 3 portions of water. The MTBE layer was concentrated to give the desired compound.

7-OSiEt$_2$(O-t-Bu)-baccatin III (31):

Using the general procedure, 11 (0.1 g, 0.14 mmol) was reacted with LHMDS (0.178 ml, 0.175 mmol) and AcIm (55 mg, 0.49 mmol) in THF (1 ml) for 72 h to give 31 (99 mg) in 94% yield.

7-OSi(i-Pr$_2$)(OMe)-baccatin III (34):

(i) Using the general procedure, 15 (12.65 g) was reacted with LHMDS (18 ml, 18 mmol) and AcIm (3.04 g, 27.6 mmol) in DMF (114 ml) to give 34 (10.7 g) in 80% yield.

(ii) Additionally, silylation and acetylation were telescoped together to produce 34 directly from 1:

1 (10 g, 18.4 mmol) and imidazole (3.75 g, 55.2 mmol) were added to 70 ml of DMF. The resulting solution was cooled to −10° C. and diisopropyldichlorosilane (4.31 ml, 23.9 mmol) was added. The reaction mixture was stirred at −10° C. until HPLC indicates <1.5% of 10-DAB remains. Methanol (1.49 ml, 36.8 mmol) was added, the cooling bath was removed and the reaction was stirred for an additional hour. The reaction mixture was then poured into a 500 ml separatory funnel containing 250 mL of MTBE. The resulting organic mixture was washed with 3×80 ml portions of water, and the final organic solution was swapped into 110 ml DMP after azeotropic drying with THF. The DMF solution was then cooled to −50° C. and LiHMDS (16.56 ml, 16.56 mmol) as a solution in THF is added. The reaction mixture was stirred at <−45° C. for 15 min and then AcIm (3.04 g, 27.6 mmol) was added as a solid and the reaction mix was allowed to warm to <−27° C. When HPLC analysis indicates less than 1.2% of 15 remains, methanol (2.23 ml, 55.2 mmol) was added and the reaction stirred for 10 min. Acetic acid (1.7 ml, 29.5 mmol) was then added, the cooling source removed, and stirring was continued for 15 min. The reaction mixture was then poured into 250 ml of MTBE and the resulting organic layer was washed with 3×100 ml portions of water. The rich MTBE solution was reduced to 50 ml in volume, and 35 ml of toluene is added. The remaining MTBE was distilled off under reduced pressure, and the final toluene volume is adjusted to 30–35 ml. The toluene solution was heated to 90° C. and 100 ml of heptane was added to induce crystallization. The crystal slurry was allowed to cool to ambient temperature, after which it was cooled to 0° C. in an ice bath and stirred for 2 h. The crystal slurry was vacuum filtered, the filter cake was washed with 2×20 ml portions of heptane the product was dried at 50° C. for 24 h under house vacuum. The yield of 34 is 81.5%, 10.961 g. PMR (CDCl$_3$); δ7.95–7.30 (m, 5H), 6.39 (s, 1H), 5.49 (d, 1H, J=7.2), 4.81 (d, 1H, J=10.8), 4.68 (br s, 1H), 4.52 (dd, 1H, J=7.2, 10.8), 4.15 (d, 1H, J=8.3), 4.01 (d, 1H, J=8.3), 3.75 (d, 1H, J=7.2), 3.38 (s, 3H), 2.52 (m, 1H), 2.14–2.11 (m, 5H), 2.06 (s, 3H), 2.01 (s, 3H), 1.94 (m, 1H), 1.85–1.78 (m, 1H), 1.57 (s, 3H), 1.05 (s, 3H), 0.92–0.82 (m, 18H).

7-OSi(i-Pr$_2$)(OEt)-baccatin-III (35):

Using the general procedure, 16 (0.352 g, 0.5 mmol) was reacted with LHMDS (0.5 ml, 0.3 mmol) and AcIm (0.138 g, 1.25 mmol) in THF (6 ml) for 4 h to give 35 (0.365 g) in 98% yield.

7-OSi(i-Pr)$_2$(OH)-baccatin III (36):

Using the general procedure, 19 (1.23 g, 1.83 mmol) was reacted with LHMDS (1.83 ml, 1.83 mmol) and AcIm (0.5 g, 4.57 mmol) in DMF (10 ml) for 3 h to give 36 (1.0 g) in 77% yield.

Example 3

Paclitaxel from the BMOP route:

LiHMDS in THF (1M, 43 ml, 0.043 mmol) was added to a stirred solution of 7-OSiEt$_2$(OCH$_2$CF$_3$)-baccatin-III (32, 30.2 mg, 0.039 mmol) in dry THF (1.5 ml) at −55° C. under argon. After 5 min of stirring, BMOP ((3R-cis)-Benzoyl-3-(1-methoxy-1-methylethoxy)-4-phen-yl-2-azetidinone) (17 mg, 0.05 mmol) in dry THF (0.5 ml) was charged over 2 min to the reaction mixture at −55° C. and stirred for 5 min. The reaction flask was removed from the cryocooler and placed in an ice bath and stirred for 4.7 h. HPLC showed a 86.4% conversion to 39. A solution of TFA (0.049 g, 0.43 mmol), water (0.252 ml, 14 mmol) and AcOH (0.822 ml, 14.35 mmol) was added and hydrolyzed the reaction mixture for 17 h. The reaction mixture was evaporated to a residue, which was purified by silica gel chromatography using hexane:EtOAc (2:3) to provide 24.2 mg of paclitaxel (HI: 84% with 12.2% of baccatin-III).

Compound 41:

A mixture of 7-OSiEt$_2$(OCH$_2$CF$_3$)-baccatin-III (32, 83 mg, 0.11 mmol), (4S-trans)-4,5-Dihydro-2,4-diphenyl-5-oxazolecarboxylic acid (4, 34.5 mg, 0.129 mmol), and DMAP (14.1 mg, 0.115 mmol) in dry toluene (2 ml) was stirred for 3 min under argon. DCC (26.7 mg, 0.13 mmol) was added at once and stirring was continued at room temperature. As HPLC showed 7.9% of unreacted starting material after 3.25 h, another portion of DCC (8 mg, 0.04 mmol) was added and stirring was continued another hour. As the reaction was completed as per HPLC analysis, the reaction was diluted with MTBE (15 ml) and washed with half-saturated NaHCO$_3$ (5 ml), water (5 ml), and brine (5 ml). The organic phase was dried over Na$_2$SO$_4$ and evaporated to a solid product (0.179 g), which was purified by silica gel chromatography using hexane:EtOAc (35:65) to furnish 41 (70 mg) in 63.8% yield.

Compound 42:

Using the procedure described for 41, 7-OSiEt$_2$(OCH$_2$CF$_2$CF$_3$)-baccatin-III (33, 93 mg, 0.113 mmol) was coupled with (4S-trans)-4,5-Dihydro-2,4-diphenyl-5-oxazolecarboxylic acid (4, 36.2 mg, 0.135 mmol) in the presence of DMAP (14.8 mg, 0.12 mmol) and DCC (28.5 mg, 0.138 mmol) in toluene (2 ml) for 3.25 h to furnish 42 (81 mg) in 66.8% yield.

Compound 43:

(4S-trans)-4,5-Dihydro-2,4-diphenyl-5-oxazolecarboxylic acid (4, 4.39 g, 16.43 mmol), DMAP (0.552 g, 4.52 mmol) and anhydrous toluene (82 ml) were added to a three neck flask equipped with a distillation setup. The resulting slurry was azeotropically distilled to remove methanol present in 4. After cooling to room temperature under argon, 34 (10 g, 13.68 mmol) was charged and the beaker was washed with 3.2 ml of toluene. After 5 min, a solution of DCC (3.4 g 16.48 mmol) in toluene (12.8 ml) was added at once and the flask was rinsed with toluene (3.2 ml). The resulting reaction mixture was stirred at room temperature for 3 h. HPLC confirmed the absence of starting material (34) and the presence of 43 (HI: 85.2%). The reaction was quenched with AcOH (0.2 ml, 3.49 mmol) and stirred for 0.5 h. EtOAc (100 ml) was added and cooled to 0° C. for 0.5 h while stirring. The reaction mixture was filtered through a sintered funnel (porosity: 10–20 micron) containing celite (#521, 1.5 g) and the DCU-celite cake was washed with cold EtOAc (3° C., 33.4 ml). The combined filtrate was transferred into a separatory funnel and the filtration flask was rinsed with EtOAc (25 ml). The organic phase was washed with 10% KH$_2$PO$_4$ (2×100 ml), 10% NaHCO$_3$ (100 ml) and water (100 ml), exchanged with IPA and crystallized to give 43 in 86% yield. PMR (CDCl$_3$): δ8.1 (d, 2H), 7.95 (d, 2H), 7.43–7.52 (m, 2H), 7.36 (t, 4H), 7.22–7.27 (m, 5H), 6.36 (s, 1H), 6.06 (t, 1H), 5.56 (d, 1H), 5.47 (d, 1H), 4.81–4.84 (m, 2H), 4.53 (dd, 1H), 4.17 (d, 1H), 4.02 (d, 1H), 3.73 (d, 1H) 3.38 (s, 3H), 2.52–2.60 (m, 1H), 2.1–2.28 (m, 1H), 2.11–2.17 (m, 1H), 2.01 (s, 3H), 1.95 (s, 3H), 1.59 (s, 3H), 1.11 (s, 3H), 1.06 (s, 3H), 0.83–0.93 (m, 14H).

Paclitaxel from 43:

A solution of TFA (4.98 ml)/AcOH (20 ml)/H$_2$O (19.12 ml) was added to a stirred solution of 43 (10 g, 10.2 mmol) in AcOH (84 ml) and stirring was continued for 24 h. HPLC confirmed the completion of the reaction and the formation of 2'-OBz-paclitaxel. The reaction was quenched with sodium acetate (5.82 g) in water (20.7 ml) and diluted with CH$_2$Cl$_2$ (94.4 ml) and water (64.6 ml). The phases were separated. The aq phase was extracted once with CH$_2$Cl$_2$ (64.6 ml). The combined CH$_2$Cl$_2$ phases were washed with water (129.2 ml) and treated with triethylamine (19.12 ml) at 20° C., while cooling in an ice-water bath. After 1 h at room temperature, the reaction was complete according to HPLC analysis. The reaction mix was quenched with a solution of conc. H$_2$SO$_4$ (16.2 ml) in water (145.4 ml) at 20° C. The organic phase was separated and washed twice with water (129.2 ml) and concentrated. The resulting rich solution was co-evaporated with IPA (3×100 ml) and crystallized to provide a 76.3% yield of paclitaxel. PMR (CDCl$_3$): δ8.06 (dd, 2H), 7.67 (dd, 2H), 7.52–7.57 (m, 1H), 7.26–7.46 (m, 10H), 6.93 (d, 1H), 6.20 (s, 1H), 6.16 (t, 1H), 5.71 (dd, 1H), 5.60 (d, 1H), 4.88 (d, 1H), 4.72 (dd, 1H), 4.30–4.36 (m, 1H), 4.24 (dd, 1H), 4.12 (dd, 1H), 3.72 (d, 1H), 3.51 (d, 1H), 2.43–2.52 (m, 1H), 2.41 (d, 1H), 2.32 (s, 3H), 2.30–2.20 (m, 2H), 2.17 (s, 3H), 1.77–1.85 (m, 1H), 1.61 (s, 3H), 1.57 (s, 3H), 1.17 (s, 3H), 1.07 (s, 3H).

Paclitaxel from 41:

Using the above procedure, 41 (65 mg, 0.06 mmol) was treated with TFA (32 μl), AcOH (0.65 ml) and water (0.166 ml) at room temperature for 6 h followed by TEA (0.180 ml, 1.29 mmol) for 1.5 h to give crude paclitaxel (53 mg, 97.4%, HI: 98.3%). This on crystallization from IPA (0.92 ml) afforded paclitaxel (21 mg, HI: 100%) in 38.6% yield.

Paclitaxel from 42:

Using the above procedure, 42 (50 mg, 0.047 mmol) was treated with TFA (23.5 μl), AcOH (0.478 ml) and water (0.122 ml) at room temperature for 6.75 h followed by TEA (0.266 ml, 1.91 mmol) for 3.25 h to give crude paclitaxel (35 mg, 97.4%, HI: 98.3%). This on silica gel chromatography using hexane:EtOAc (35:65) furnished paclitaxel (30.5 mg) in 76.4% yield.

What is claimed is:

1. A process for the synthesis of paclitaxel starting from 10-deacetylbaccatin-III using a protecting group having the formula —Si(R)$_2$(OR'), at the 7-O-position, where R is Me, Et, i-Pr, Bu, and Ph, and where R' is Me, Et, Pr, i-Pr, t-Bu, CH$_2$CF$_3$, CH$_2$CF$_2$CF$_3$, CH(CF$_3$)$_2$ and H.

2. The process for the synthesis of paclitaxel starting from 10-deacetylbaccatin-III as recited in claim 1, wherein said protecting group at the 7-O-position is diisopropylmethoxysilyl.

3. A process for the synthesis of paclitaxel from 10-deacetylbaccatin-III, which comprises selectively silylating 10-deacetylbaccatin-III at the 7-position using a dialkyldichlorosilane, followed by the selective acetylation at the C-10-position, and the subsequent addition of a paclitaxel sidechain at the C-13 position.

4. A paclitaxel derivative having the formula:

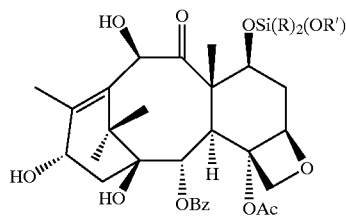

wherein

R=Me, Et, i-Pr, n-Bu, or Ph; and

R'=H, Me, Et, Pr, i-Pr, t-Bu, CH$_2$CF$_3$, CH$_2$CF$_2$CF$_3$, or CH(CF$_3$)$_2$.

5. A paclitaxel derivative according to claim 4, having the formula:

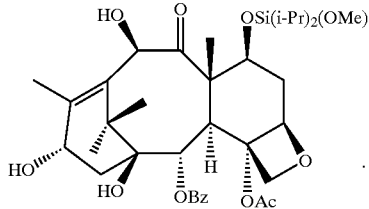

6. A paclitaxel derivative having the formula:

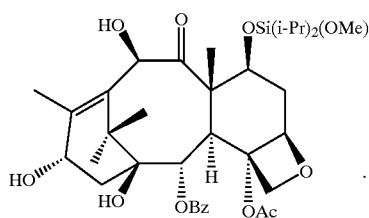

7. A paclitaxel derivative having the formula:

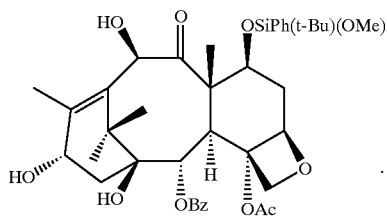

8. A paclitaxel derivative having the formula:

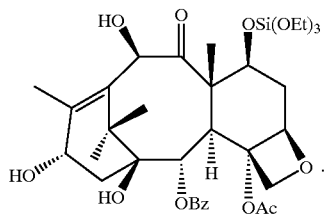

9. A process for the production of paclitaxel from an intermediate compound having the general formula and numbering:

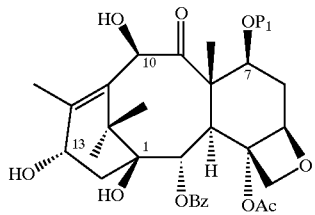

wherein $P_1$ is a protecting group, and which comprises the steps of selective acetylation at the C-10 position, followed by the coupling of a paclitaxel sidechain at C-13, and subsequently deprotecting at the C-7 position to replace $P_1$ with a H.

10. The process according to claim 9, wherein said protecting group $P_1$ is of the general formula —Si(R)$_2$(OR'), where R is Me, Et, i-Pr, Bu, and Ph, and where R' is Me, Et, Pr, i-Pr, t-Bu, CH$_2$CF$_3$, CH$_2$CF$_2$CF$_3$, CH(CF$_3$)$_2$ and H.

11. The process according to claim 10, wherein said protecting group is diisopropylmethoxysilyl.

12. A process for synthesizing paclitaxel of the formula:

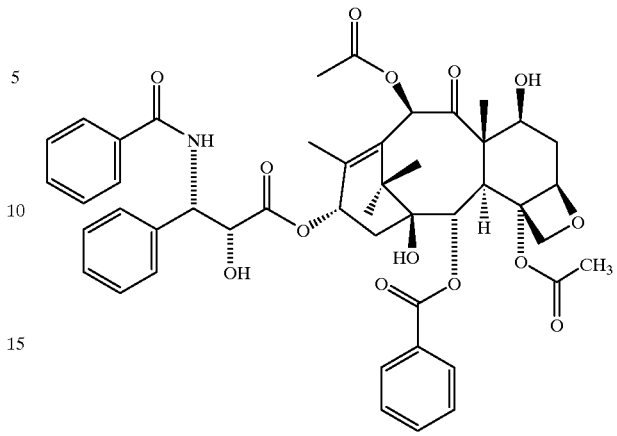

comprising the steps of:
a. treating a solution of 10-deacetylbaccatin-III having the formula:

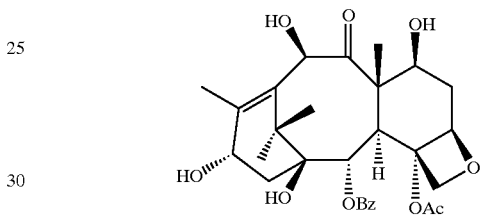

with a diethyldichlorosilane protecting group in a solvent to form a 7-O-protected 10-deacetylbaccatin-III derivative having the formula:

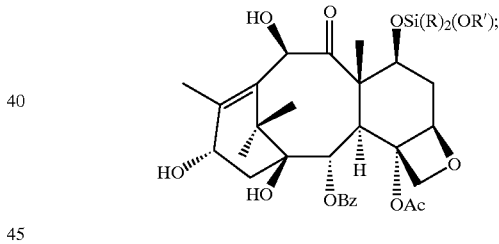

b. selectively acetylating the hydroxyl at the C-10 position to form a 7-O-protected baccatin-III derivative having the formula:

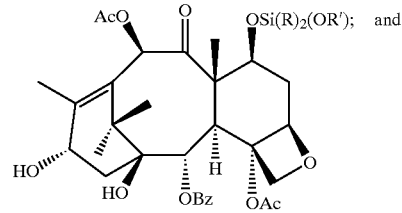

c. reacting the 7-O-protected baccatin-III derivative with a protected paclitaxel sidechain in a solvent, such that said sidechain is coupled with said 7-O-protected baccatin-III derivative at the C-13 position.

13. The process according to claim 12, wherein said protecting group at the C-7 position of the a 7-O-protected 10-deacetylbaccatin-III derivative is diisopropylmethoxysilyl.

* * * * *